US007662978B2

(12) United States Patent
Xie et al.

(10) Patent No.: US 7,662,978 B2

(45) Date of Patent: Feb. 16, 2010

(54) DIBENZYLIDENE SORBITOL (DBS)-BASED COMPOUNDS, COMPOSITIONS AND METHODS FOR USING SUCH COMPOUNDS

(75) Inventors: Chunping Xie, Boiling Springs, SC (US); Lee R. Rieth, Spartanburg, SC (US); Todd D. Danielson, Moore, SC (US)

(73) Assignee: Milliken & Company, Spartanburg, SC (US)

(*) Notice: Subject to any disclaimer, the term of this patent is extended or adjusted under 35 U.S.C. 154(b) by 219 days.

(21) Appl. No.: 11/700,740

(22) Filed: Jan. 31, 2007

(65) Prior Publication Data

US 2007/0249850 A1 Oct. 25, 2007

Related U.S. Application Data

(60) Provisional application No. 60/794,788, filed on Apr. 24, 2006.

(51) Int. Cl.
*C07D 323/04* (2006.01)
*C08K 5/00* (2006.01)

(52) U.S. Cl. .................................. 549/364; 524/108

(58) Field of Classification Search ................ 549/314; 524/108

See application file for complete search history.

(56) References Cited

U.S. PATENT DOCUMENTS

| | | | | |
|---|---|---|---|---|
| 3,721,682 | A | 3/1973 | Murai et al. | 260/340.7 |
| 4,016,118 | A | 4/1977 | Hamada et al. | 260/17.4 |
| 4,314,039 | A | 2/1982 | Kawai et al. | 525/1 |
| 4,371,645 | A | 2/1983 | Mahaffey, Jr. | 524/108 |
| 4,514,534 | A | 4/1985 | DiNardo | 524/108 |
| 4,532,280 | A | 7/1985 | Kobayashi et al. | 524/108 |
| 4,552,687 | A | 11/1985 | Beacham et al. | 252/500 |
| 4,575,563 | A | 3/1986 | Gunkel | 568/14 |
| 4,954,291 | A | 9/1990 | Kobayashi et al. | 252/316.1 |
| 5,049,605 | A | 9/1991 | Rekers | 524/108 |
| 5,106,999 | A | 4/1992 | Gardlik et al. | 549/364 |
| 5,135,975 | A | 8/1992 | Rekers | 524/108 |
| 5,198,484 | A | 3/1993 | Mannion et al. | 524/108 |
| 5,310,950 | A | 5/1994 | Mannion et al. | 549/364 |
| 5,420,220 | A | 5/1995 | Cheruvu et al. | 526/348.1 |
| 5,792,560 | A | 8/1998 | Friedman et al. | 428/441 |
| 5,973,043 | A | 10/1999 | Miley et al. | 524/199 |
| 6,022,140 | A | 2/2000 | Fraden et al. | 374/158 |
| 6,159,608 | A | 12/2000 | Friedman et al. | 428/442 |
| 6,423,170 | B1 | 7/2002 | Friedman et al. | 156/244.11 |
| 6,562,890 | B2 | 5/2003 | Dotson | 524/396 |
| 6,599,971 | B2 | 7/2003 | Dotson et al. | 524/394 |
| 7,262,236 | B2 * | 8/2007 | Xie et al. | 524/108 |
| 2005/0239926 | A1 | 10/2005 | Xie et al. | 524/90 |
| 2005/0239928 | A1 | 10/2005 | Xie et al. | 524/108 |

FOREIGN PATENT DOCUMENTS

| | | |
|---|---|---|
| WO | WO 95/13317 | 5/1995 |
| WO | WO 2005/035598 | 4/2005 |
| WO | WO 2005/108479 A2 | 11/2005 |
| WO | WO 2005/111134 A2 | 11/2005 |

OTHER PUBLICATIONS

Commonly assigned U.S. Patent application entitled "Acetal based compositions", U.S. Appl. No. 10/831,920 to Milliken & Company, filed Apr. 26, 2004. Our docket No. 5731.

Commonly assigned U.S. Patent application entitled "Method of nucleating a polyolefin composition with acetal-based compounds", U.S. Appl. No. 10/893,633 to Milliken & Company, filed Jul. 16, 2004. Our docket No. 5731A.

Synthesis of a branched-chain inosose derivative, a versatile synthon of N-substituted valiolamine derivatives; J. Org. Chem. 1991, 57,3642-3650.

JACS Articles; Universal NMR databases for contiguous polyols; J. AM. Chem. Soc. 2003, 125,14379-14393.14379.

Multicarbon chain extension of sugars through acetylenic intermediates. A Hexadecitol; Department of Chemistry, University of Washington, Seattle, Washington 98105; received Dec. 1, 1970.

Surface haze and surface morphology of blown film compositions; Rajen Patel, Varun Ratta, Pepe Saavedra, Jing Li. Dow Plastics, The Dow Chemical Company, Freeport, Texas 77541, (2000).

ASTM Designation: D1003-00; Standard test method for haze and luminous transmittance of transparent plastics; EDT 2005.

J. American Chemical Society- 1991, 113,6674-6675—Carbon-Carbon bond formation in aqueous ethanol: Diastereoselective transformation of unprotected carbohydrates to higher carbon sugars using allyl bromide and tin metal. Received Apr. 5, 1991.

J. Org. Chem. 1993, 58, 5500-5507—Tin-and indium-mediated allylation in aqueous media: Application to unprotected carbohydrates. Received Mar. 2, 1993.

JOC Article—Double diastereoselection in aldol reactions mediated by dicyclohexylchloroborane between L-erythrulose derivatives and chiral aldehydes. The Felkin-Anh versus cornforth dichotomy. J. Alberto Marco, Miguel Carda, Santiago Diaz-Oltra, Juan Murga, Eva Falomir, and Harald Roeper. Received Aug. 6, 2003.

* cited by examiner

*Primary Examiner*—Janet L. Andres
*Assistant Examiner*—Raymond Covington
(74) *Attorney, Agent, or Firm*—Robert M. Lanning

(57) ABSTRACT

The present invention relates to dibenzylidene sorbitol ("DBS")-based compounds. The compounds of this invention are particularly advantageous in that they are characterized by one or more of improved transparency (reduced haze), reduced yellowing and/or improved organoleptics (taste). According to one embodiment, the present invention provides a disubstituted DBS-based compound having an allyl group or a propyl group substituted on the first carbon of the sorbitol chain. The present invention also relates to compositions comprising such DBS-based compounds and methods for using them.

11 Claims, No Drawings

DIBENZYLIDENE SORBITOL (DBS)-BASED COMPOUNDS, COMPOSITIONS AND METHODS FOR USING SUCH COMPOUNDS

CROSS REFERENCE TO RELATED APPLICATIONS

This application is related to and claims priority from previously filed U.S. provisional application Ser. No. 60/794,788 filed on Apr. 24, 2006 for "DIBENZYLIDENE SORBITOL (DBS)-BASED COMPOUNDS, COMPOSITIONS AND METHODS FOR USING SUCH COMPOUNDS".

FIELD OF THE INVENTION

The present invention relates to dibenzylidene sorbitol ("DBS")-based compounds. The compounds of this invention are particularly advantageous in that they are characterized by one or more of improved transparency (reduced haze), yellowing and improved organoleptics.

BACKGROUND OF THE INVENTION

Derivatives of acetals of polyhydric alcohols are useful in several applications, including, for example, as nucleating or clarifying agents for polymer resins and as gelling and thickening agents for organic liquids. DBS-based compounds are useful in such applications.

Nucleating or clarifying agents have been used to reduce haze in articles manufactured from crystalline polyolefin resins. Representative acetals of sorbitol and xylitol, which have been employed as nucleating or clarifying agents, are described in Hamada, et al., U.S. Pat. No. 4,016,118, dibenzylidene sorbitols; Kawai, et al., U.S. Pat. No. 4,314,039, di(alkylbenzylidene) sorbitols; Mahaffey, Jr., U.S. Pat. No. 4,371,645, di-acetals of sorbitol having at least one chlorine or bromine substituent; Kobayashi, et al., U.S. Pat. No. 4,954,291, distribution of diacetals of sorbitol and xylitol made from a mixture of dimethyl or trimethyl substituted benzaldehyde and unsubstituted benzaldehyde. U.S. Pat. No. 5,049,605 to Rekers et al. discloses bis(3,4-dialkylbenzylidene) sorbitols. As an example of one type of clarifier, 1,3-O-2,4-bis(3,4-dimethylbenzylidene) sorbitol (hereinafter DMDBS), available from Milliken Chemical under the trade name Millad® 3988, provides clarification for target polypropylenes and other polyolefins.

Changes among various substituted groups in DBS-based compounds may have a significant impact upon the performance of the compound in plastics. In particular, substitution of various groups upon the benzyl ring portion(s) of DBS-based compounds may have a significant impact upon the suitability of such compounds as nucleating or clarifying agents. Accordingly, efforts in the past have been directed to modifying the substitution pattern of the benzylidene ring substituent(s).

Published patent applications US 2005-0239926A1 and US 2005-0239928A1 to Xie et al. disclose acetal-based compositions useful as nucleating or clarifying agents. These references disclose, in part, that dibenzylidene sorbitol derivatives substituted on the first carbon of the sorbitol chain are particularly effective clarifying agents.

The percent haze of polyolefin articles is a common measure of the level of clarity that a nucleating or clarifying agent imparts to polyolefin articles that employ such an agent. In general, a reduction of only a single percent (or even a fraction of a percent) in haze can be very significant in the industry. Thus, there is a continual endeavor in the plastic additives industry to find nucleating or clarifying agent compounds that will afford the lowest amount of haze. The leading commercial clarifying agent, Millad® 3988, provides about 7-8% haze in a 50 mils (1.27 millimeters) injection molded random copolymer polypropylene article. It has long been the objective of the industry to develop a clarifying agent that would provide reduced levels of haze under the same conditions and at the same concentration levels.

Low haze is not the only important factor in determining the suitability of a plastic additive. Poor thermal stability may cause undesirable yellowing and plate-out at high processing temperatures. Such yellowing is undesirable.

The nucleating or clarifying agent must not impart excessive undesirable taste to the plastic articles into which it is incorporated. Thus, nucleating or clarifying agents that provide reduced organoleptic problems or issues are desirable. "Organoleptic" refers to taste that undesirably may be transferred to a polymeric food or drink storage container by a nucleating or clarifying agent compound incorporated into the plastic.

These noticeable problems have created a long-felt need in the polyolefin clarifier industry to provide such compounds that do not exhibit these problems and provide excellent clarity for the target polyolefin articles themselves. To date, the best known compounds for this purpose remain those noted above.

DETAILED DESCRIPTION OF THE INVENTION

This invention provides novel nucleating or clarifying agent compounds demonstrating, unexpectedly, one or more of the characteristics of improved haze, yellowing and organoleptics. According to one embodiment, a dibenzylidene sorbitol (DBS) derivative provides a disubstituted DBS-based compound having an allyl group or a n-propyl group substituted on the first carbon of the sorbitol chain (C-1 position). The present invention also relates to compositions comprising such DBS-based compounds and methods for using them. The compounds of the invention may be represented by formula I:

I

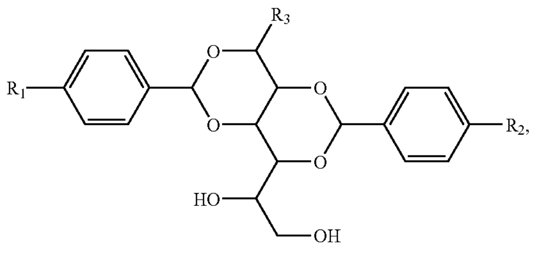

wherein $R_1$ and $R_2$ are independently selected from the group consisting of: $CH_3CH_2CH_2$—(i.e. n-propyl) and $CH_3CH_2CH_2O$—(i.e. n-propoxy); and wherein $R_3$ is independently selected from the group consisting of: —$CH_2CH_2CH_3$ (n-propyl) and —$CH_2$—$CH{=}CH_2$ (allyl).

Applicants studied a number of nucleating or clarifying agents, including those described in US 2005-0239926A1 and US 2005-0239928A1 to Xie et al. Compounds of formula I were found to have unexpectedly improved performance characteristics, i.e., reduced haze, organoleptics and/or yellowing, relative to other nucleating or clarifying agents tested, including some that were closely related in structure.

In one embodiment of the invention, the compound of formula I is provided, wherein $R_3$ is a n-propyl group ($—CH_2CH_2CH_3$). In an alternative embodiment, $R_3$ is an allyl group ($—CH_2CH{=}CH_2$).

In one embodiment of the invention, $R_1$ and $R_2$ are n-propyl. In alternate embodiment, $R_1$ and $R_2$ are n-propoxy.

In another embodiment of the invention, $R_1$ and $R_2$ are the same; that is, the compound of formula I is symmetric. In another embodiment, $R_1$ and $R_2$ are different; that is, the compound of formula I is asymmetric.

In another embodiment of the invention, $R_3$ is allyl and $R_1$ and $R_2$ are independently selected from the group consisting of n-propyl and n-propoxy.

In another embodiment of the invention, $R_3$ is n-propyl and $R_1$ and $R_2$ are independently selected from the group consisting of n-propyl and n-propoxy.

According to one embodiment of the invention, the compound of formula I is Compound 1:

Compound 1

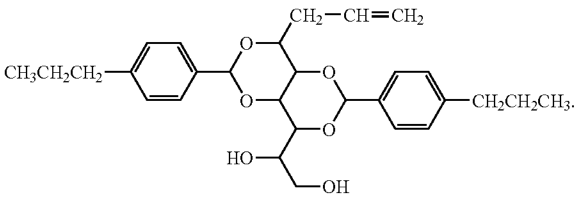

According to another embodiment of the invention, the compound of formula I is Compound 2:

Compound 2

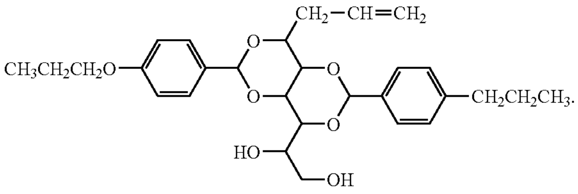

According to another embodiment of the invention, the compound of formula I is Compound 3:

Compound 3

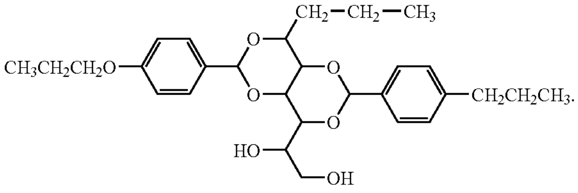

According to another embodiment of the invention, the compound of formula I is Compound 4:

Compound 4

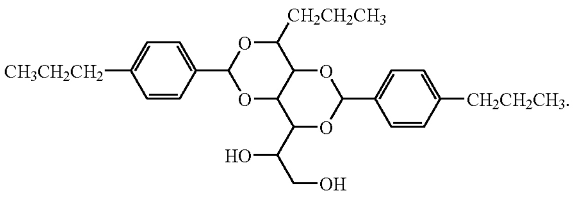

The compounds of formula I of the present invention are useful in several applications, including, for example, as nucleating or clarifying agents for polymer resins and as gelling and thickening agents for organic liquids.

According to another embodiment of the invention, the present invention provides nucleating or clarifying compositions comprising a compound of formula I.

According to one embodiment of the invention, the nucleating or clarifying compositions comprise a mixture of compounds of formula I. In one embodiment, such a composition comprises a mixture of asymmetric compounds of formula I. In another embodiment, the nucleating or clarifying composition comprises a mixture of symmetric compounds of formula I.

In one embodiment, the nucleating or clarifying composition comprises Compound 1. In another preferred embodiment, the nucleating or clarifying composition comprises Compound 2. In another embodiment, the nucleating composition or clarifying comprises Compound 3. In yet another embodiment, the nucleating or clarifying composition comprises Compound 4.

According to an embodiment, the present invention provides a method of nucleating an olefin polymer, comprising the step of combining an olefin polymer with a compound of formula I.

According to another embodiment, the present invention provides a polyolefin composition comprising a compound of formula I and an olefin polymer.

Olefin polymers that may be utilized in this invention include polymers and copolymers of aliphatic mono-olefins containing from 2 to about 6 carbon atoms, which have an average molecular weight of from about 10,000 to about 2,000,000, preferably from about 30,000 to about 300,000, such as, for example, polyethylene, including linear low density polyethylene, low density polyethylene and high density polyethylene, polypropylene, crystalline ethylene/propylene copolymer (random or block), poly(1-butene) and polymethylpentene.

Examples of other olefin polymers which may be utilized in this invention include, for example, polyester, poly(ethylene terephthalate) (PET) and poly(butylene terephthalate) and polyamide, including nylon 6 and nylon 6,6, poly(phenylene sulfide), syndiotactic polystyrene and polyketones having carbonyl groups in their backbone.

In a desirable embodiment of the invention, the polyolefin composition comprises polypropylene.

According to one embodiment of the invention, the polyolefin composition comprises a compound of formula I at a concentration of from about 0.005 to about 3 weight percent, preferably from about 0.01 to about 1 weight percent and more preferably from about 0.025 to about 0.5 weight percent, and yet even more preferably from about 33 weight percent or less, as in a concentrated masterbatch.

According to another embodiment of the invention, the polyolefin composition comprises a compound of formula I at a concentration of up to 50 weight percent, as in the case of a "masterbatch" composition. In a preferred embodiment, the polyolefin composition could comprise more than one olefin polymer.

In various embodiments, compounds of formula I of the invention provide improved transparency (reduced haze) to the polyolefin compositions into which they are incorporated. In alternate embodiments, compounds of formula I provide improved yellowing to the polyolefin compositions. In yet another embodiment, compounds of formula I provide improved transparency, yellowing and organoleptics to the polyolefin compositions.

According to another embodiment of the invention, the polyolefin compositions are molded or extruded to form various polymeric articles of manufacture.

According to one embodiment of the present invention, the polyolefin composition is extruded multiple times before being processed into a finished article. Suitable methods for extruding the polyolefin composition include, but are not limited to, injection molding, extrusion blow molding, injection blow molding, stretch blow molding, compression molding, rotational molding, profile extrusion, sheet extrusion, thermal forming, film extrusion, and film extrusion with orientation.

Synthesis Procedures

The compounds of formula I may be synthesized by a variety procedures. Such procedures may be those described herein or those known in the art. Generally, such procedures employ the reaction of one mole of substituted alditol (such as allyl-sorbitol, n-propyl-sorbitol, allyl-xylitol, n-propyl-xylitol and the like) with 2 moles of aldehyde in the presence of an acid catalyst (inorganic acid such as hydrochloric acid or organic acid such as p-toluenesulfonic acid (pTSA)). Further, an organic solvent is employed that is miscible with water (such as lower alkyl alcohols, N-N-dimethylformamide, or acetic acid) at room temperature.

One method that can be employed to prepare the compounds of formula I is described in U.S. Pat. No. 5,106,999 to Gardlik et al., which is hereby incorporated by reference.

Methods to synthesize alditols of varying chain length are disclosed in Kim, Gordon, Schmid, and Whitesides, *Tin and Indium Mediated Allylation in Aqueous Media: Application to Unprotected Carbohydrates*, J. Org. Chem, 5500-5507, 58 (1993) and in Whitesides, *Journal of the American Chemical Society,* 113, 6674-6675 (1991). Whitesides has referred to the reaction of glucose with allyl bromide/tin.

According to one embodiment, synthetic schemes for making the compounds are depicted below. One of skill in the art will recognize that these schemes are merely exemplary, and that other methods may be used to prepare the compounds of formula I.

Scheme 1 illustrates a process for making intermediates C and D. In Scheme 1, intermediate C is prepared by reacting a sugar A and an alkenyl group B.

Scheme 1

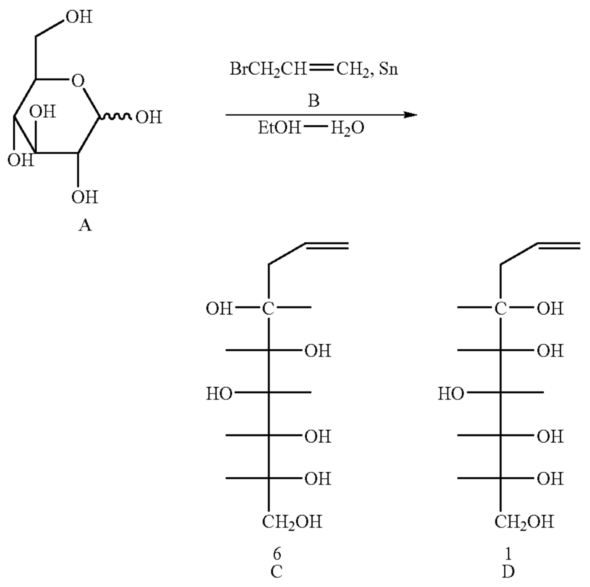

A

6
C

1
D

Scheme 2 illustrates a representative example of a method for making compounds of formula I wherein $R_3$ is allyl or propyl.

When $R_3$ is allyl, as shown in Scheme 2, a polyhydric alcohol A and an allyl containing group B are provided. In the next step, the polyhydric alcohol A and the allyl-containing group B are reacted to form a first allyl-containing compound C. Then, compound C is reacted in a condensation reaction with a substituted benzaldehyde F to form compound G.

In an alternate embodiment, $R_3$ is propyl. In this method, a polyhydric alcohol A and an allyl group B are employed. The polyhydric alcohol A and an allyl-containing group B are reacted to form compound C. The allyl-containing compound C is reduced to form an n-propyl substituted compound E, which is then reacted in a condensation reaction with a substituted aromatic aldehyde F to form compound H.

Scheme 2

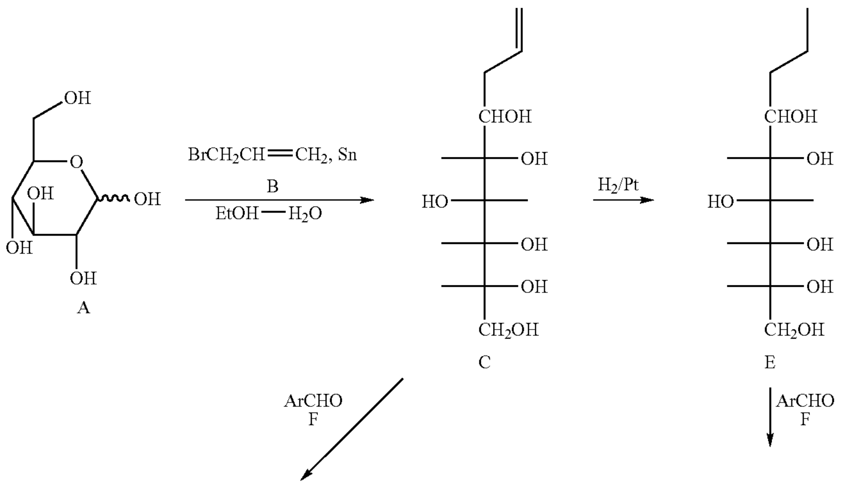

A

C

E

-continued

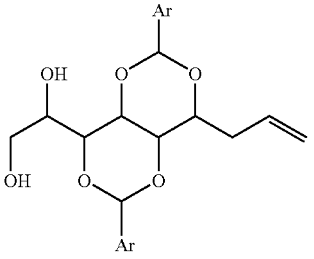

G

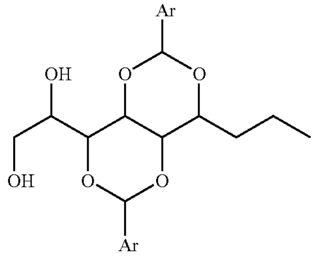

H

Thus, the present invention provides a method for making a compound of formula I, wherein $R_3$ is allyl, comprising the steps of (a) providing a polyhydric alcohol and an allyl group; (b) reacting the polyhydric alcohol and the allyl group to form a first allyl-containing compound; (c) reacting the first allyl-containing compound in a condensation reaction with a substituted benzaldehyde.

In another embodiment, the present invention provides a method for making a compound of formula I, wherein $R_3$ is n-propyl, comprising the steps of (a) providing a polyhydric alcohol and an allyl group, (b) reacting said polyhydric alcohol and said allyl group to form a first allyl-containing compound (c) reducing said allyl-containing compound to form an n-propyl substituted compound, and (d) reacting in a condensation reaction said n-propyl substituted compound with a substituted aromatic aldehyde.

As shown in Scheme 2, compounds of formula I maybe obtained by a condensation reaction using a suitable benzaldehyde. One of skill in the art will recognize that the condensation reaction produces a mixture of diacetals (compound of formula I), triacetals and monacetals. Although it may not always be necessary to remove the triacetals and monacetals (particularly if they are present in very low proportions) prior to incorporation of the compound of formula I into the polyolefin composition, it may be desirable to do so and such purification may serve to enhance the transparency of the resin produced thereby.

According another embodiment of the invention, purification of the compound of formula I may be accomplished by removal of any present tri-acetals by the extraction thereof with a relatively non-polar solvent. As one non-limited example, the composition of the present invention comprises a compound of formula I in which the composition is at least about 95-98 percent pure, depending upon the application.

Reference now will be made to various alternative embodiments of the invention, one or more examples of which are set forth below. Each example is provided by way of explanation of the invention, not as a limitation of the invention. It will be apparent to those skilled in the art that various modifications and variations can be made in this invention without departing from the scope or spirit of the invention.

EXAMPLE 1

1-Allyl Sorbitol

A three liter three-necked round bottom flask, equipped with heating mantle, stirrer, nitrogen inlet, and condensor, was charged with 900 mL of ethanol, 150 mL of water, 180 g (1.00 mole) of D-glucose, 119 g (1.00 mole) of tin powder (−100 mesh), and 121 g (1.00 mole) of allyl bromide. The mixture was stirred and slowly heated at 60° C. The gray suspension was stirred at this temperature for 24 hours, in which time the reaction mixture turned a light yellow color. Heat was removed and the mixture was allowed to cool to room temperature. The reaction was neutralized to pH=7 by adding approximately 200 ml of 5M NaOH aqueous solution. The suspension was filtered to remove solids, and the yellow solution was decolorized with multiple treatments of activated carbon. The activated carbon was removed by filtration, and the solvent was removed by rotary evaporation to isolate a white syrup. Typical yield was 200 g with a threo-erythro ratio of 6:1, based on GC-MS. The 1-allyl sorbitol syrup was used without further purification.

EXAMPLE 2

Bis-1.3, 2,4-(4'-propylbenzylidene)-1-Allyl Sorbitol

Compound 1

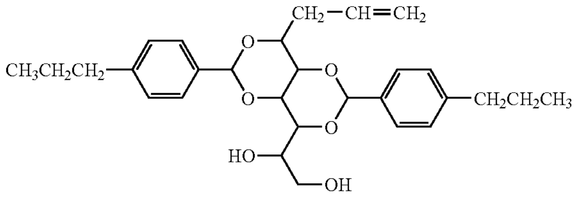

A two liter reaction kettle, equipped with a stirrer and nitrogen inlet, was charged with a solution of 48.8 g (0.22 mol) of 1-allyl sorbitol syrup in 400 ml of methanol. 97.7 g (0.44 mol) of 4-propylbenzaldehyde diethylacetal and 4.3 g of p-toluenesulfonic acid monohydrate were added to the reaction vessel. The clear solution was stirred for 24 hours, during which time a significant amount of white precipitate formed. The white powder was isolated by filtration and washed with 250 ml of 1 M NaOH aqueous solution. The white powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was dried in a vacuum oven to give 44.5 g of product, m.p. 223-225° C. The purity was above 99%, based on GC-MS. $^{1}$H NMR(500 MHz, DMSO-$d_6$, ppm): 0.86-0.90 (m, 6H, $-CH_2CH_2CH_3$), 1.53-1.61 (m, 4H, $-CH_2CH_2CH_3$), 2.41-2.44 (t, 2H, $-CH_2-CH{=}CH_2$), 2.55-2.57 (m, 4H, $-CH_2CH_2CH_3$), 3.42-4.09 (m, 7H, sugar H), 4.37-4.39 (t, 1H, $-CH_2OH$), 4.79-4.80 (d, 1H, $-CHOH$), 5.08-5.18 (q, 2H, —$CH_2CH$═$CH_2$), 5.60 (s, 1H, acetal), 5.64 (s, 1H, acetal), 5.84-5.93 (m, 1H, —$CH_2$—CH═$CH_2$), 7.17-7.21 (t, 4H), 7.34-7.37 (t, 4H).

EXAMPLE 3

Bis-1,3,2,4-(4'-propoxylbenzylidene)-1-Allyl Sorbitol

Compound 2

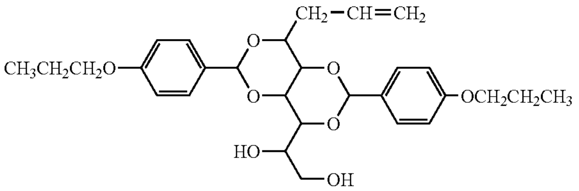

65.2 g (0.29 mol) of 1-allyl sorbitol syrup (produced in Example 1) was dissolved in 500 ml of methanol. 104 g of 4-propoxybenzaldehyde (0.63 mol) was added. The solution was brought to pH=1 with addition of acid. The reaction was stirred at room temperature for 5 hours. The resultant solid was collected by filtration and washed with aqueous KOH solution until pH>10. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was dried in a vacuum oven to give 78.5 g of product, m.p. 206-208° C. The purity was above 99%, based on GC-MS. $^1$H NMR(500 MHz, DMSO-$d_6$, ppm): 0.95-0.98 (m, 6H, —$OCH_2CH_2CH_3$), 1.68-1.76 (m, 4H, —$OCH_2CH_2CH_3$), 2.40-2.42 (t, 2H, —$CH_2$—CH═$CH_2$), 3.41-3.82 (m, 5H, sugar H), 3.90-3.93 (m, 4H, —$OCH_2CH_2CH_3$), 4.04-4.07 (m, 2H, sugar H), 4.36-4.38 (t, 1H, —$CH_2OH$), 4.78-4.79 (d, 1H, —CHOH), 5.07-5.18 (q, 2H, —$CH_2CH$═$CH_2$), 5.56 (s, 1H, acetal), 5.60 (s, 1H, acetal), 5.84-5.92 (m, 1H, —$CH_2$—CH═$CH_2$), 6.90-6.93 (t, 4H), 7.33-7.37 (t, 4H).

EXAMPLE 4

1-Propyl Sorbitol 30 g (0.135 mol) of 1-allyl sorbitol syrup (produced as in example 1) was dissolved in 300 ml ethanol. 1.0 g of platinum (5% weight on activated carbon) was added and the mixture was hydrogenated at room temperature with hydrogen pressure at 60 psi. The reaction was stopped until no hydrogen pressure drop was observed. The solid was filtered. The allyl group of the solution was completely converted to propyl group based on NMR.

EXAMPLE 5

Bis-1,3,2,4-(4'-propylbenzylidene)-1-Propyl Sorbitol

Compound 3

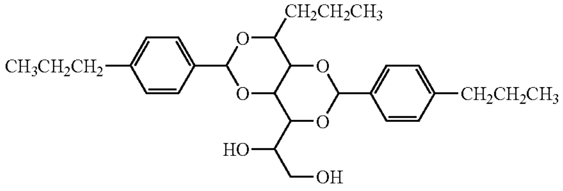

A one liter reaction kettle, equipped with a stirrer and nitrogen inlet, was charged with the propyl sorbitol ethanol solution. 40 g (0.27 mol) of 4-propylbenzaldehyde, and 2.6 g of p-toulenesulfonic acid monohydrate was added to the reaction vessel. The clear solution was stirred for 24 hours, during which time a significant amount of white precipitate formed. The white powder was isolated by filtration and washed with 250 ml of 1 M NaOH aqueous solution. The white powder was suspended in water and further neutralized to pH=7 with a small amount of NaOH. The suspension was heated to boiling, then filtered. The white powder was washed with 7×500 ml of boiling water. The washed powder dried overnight. The white powder was then stirred in 500 mL of cyclohexane, heated until boiling, filtered, and washed with 2×250 ml of boiling cyclohexane. Further purification was accomplished by using an Ace Glass 6810 Giant Soxhlet Extraction Apparatus (size F) and cellulose fiber thimble (58×170 MM OD) with 2000 ml of methanol. The white powder was slurried in 250 ml of methanol, poured into the thimble, and extracted over 5 days of reflux. The resultant extract was chilled to 5° C. and filtered to collect the white solid, which was slurried in 1000 ml of petroleum ether, filtered, and air dried. The isolated white powder was dried in a vacuum oven to give 20.1 g of product, m.p. 244-245° C. The purity was above 99%, based on GC-MS. $^1$H NMR(500 MHz, DMSO-$d_6$, ppm): 0.86-0.89 (m, 6H, Ph-$CH_2CH_2CH_3$), 0.91-0.94 (t, 3H, sugar-$CH_2CH_2CH_3$), 1.35-1.49 (m, 2H, sugar-$CH_2CH_2CH_3$) 1.54-1.60 (m, 4H, Ph-$CH_2CH_2CH_3$), 1.61-1.71 (m, 2H, sugar-$CH_2CH_2CH_3$), 2.53-2.56 (t, 4H, Ph-$CH_2CH_2CH_3$), 3.41-4.04 (m, 7H, sugar H), 4.36-4.39 (t, 1H, —$CH_2OH$), 4.78-4.79 (d, 1H, —CHOH), 5.60 (s, 1H, acetal), 5.62 (s, 1H, acetal), 7.17-7.20 (dd, 4H), 7.32-7.37 (dd, 4H).

EXAMPLE 6

Bis-1,3,2,4-(4'-propoxylbenzylidene)-1-Propyl Sorbitol

Compound 4

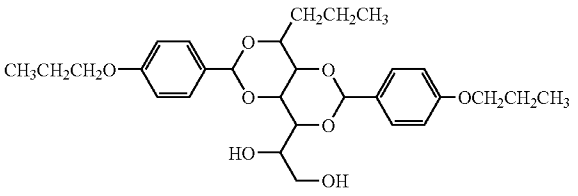

25 g (0.15 mol) of 4-propoxybenzaldehyde was added to a solution of 17.0 g (0.076 mol) of propyl sorbitol (produced in Example 4) in 200 ml of methanol, followed with 1.5 g of p-toulenesulfonic acid monohydrate. The reaction was stirred at room temperature overnight. The resultant solid was collected by filtration, washed with aqueous KOH solution until pH>10. The suspension was heated to boiling, then filtered. The white powder was washed with 7×500 ml of boiling water. The washed powder dried overnight. The white powder was then stirred in 500 mL of cyclohexane, heated until boiling, filtered, and washed with 2×250 ml of boiling cyclohexane. The isolated white powder was dried in a vacuum oven to give 22.3 g of product, m.p. 215-217° C. The purity was above 99%, based on GC-MS. $^1$H NMR(500 MHz, DMSO-$d_6$, ppm): 0.90-0.93 (t, 3H, —$CH_2CH_2CH_3$), 0.95-0.98 (m, 6H, —$OCH_2CH_2CH_3$), 1.36-1.47 (m, 2H, —$CH_2CH_2CH_3$), 1.53-1.60 (m, 2H, —$CH_2CH_2CH_3$), 1.63-1.75 (m, 4H, —$OCH_2CH_2CH_3$), 3.40-3.81 (m, 5H, sugar H), 3.90-3.93 (t, 4H, —$OCH_2CH_2CH_3$), 3.97-4.02 (m, 2H, sugar H), 4.37-4.40 (t, 1H, —$CH_2OH$), 4.79-4.80 (d, 1H, —CHOH), 5.56 (s, 1H, acetal), 5.59 (s, 1H, acetal), 6.90-6.93 (m, 4H), 7.31-7.37 (dd, 4H).

COMPARATIVE EXAMPLE 7

Bis-1,3,2,4-(4'-ethylbenzylidene)-1-Allyl Sorbitol

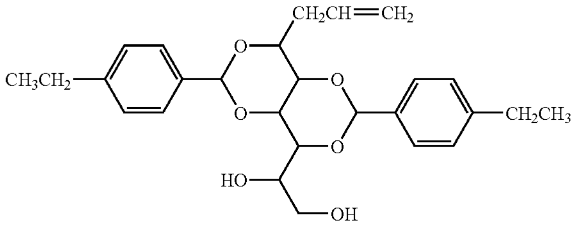

This compound was prepared according to the methods disclosed in US Patent Publication 2005-0239928A1.

COMPARATIVE EXAMPLES 8-14

A variety of allyl and proproxl substituted DBS derivatives, including examples from US 2005-0239926A1 and US 2005-0239928A1 and DBS derivatives that are most closely related structurally to the current invention were prepared according to the methods of US 20050239928A1. Structures are shown in Table 1. All derivatives had NMR consistent with the indicated structures, and purity of at least 95%, based on GC-MS.

EXAMPLE 16

Haze Comparisons of Inventive Compounds and Comparatives

Compositions containing examples 2,3,5,6 and comparative examples 7-14, were each separately mixed with 1000 grams of an 11 MFR (Melt Flow Rate) polypropylene random copolymer resin (RCP, 3% ethylene content) and standard additive package (i.e. 500 ppm Irganox 1010, 1000 ppm Irgafos 168, and 800 ppm Calcium Stearate, CaSt) using a Gardner ribbon blender for five minutes at approximately 200-220 rpm. The blend was then melt compounded on a Prism 16 mm diameter, 25:1 L/D co-rotating twin screw extruder. The melt-compounded resin was injection molded using a 40-ton Arburg AllRounder 221K to produce twenty 51 mm×76 mm×1.27 mm test plaques, which were collected in sequential order. Each resin was processed on the molder using a 230° C. flat profile barrel temperature and no back-pressure.

Millad 3988® sample was also compounded for the organoleptic study. Millad 3988® is a registered trademark of Milliken and Company of Spartanburg, S.C. Millad 3988® is a commercially distributed clarifying agent that is also known as bis(3,4-dimethylbenzylidene sorbitol)("DMDBS") and is disclosed in U.S. Pat. No. 5,049,605.

Percent haze was measured using a BYK Gardner Hazegard Plus hazemeter according to ASTM D1003. The results are reported in Table 1.

TABLE 1

Haze Values (Concentration of Clarifier = 5000 ppm)

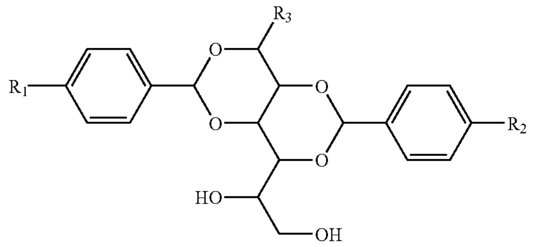

| Example # | $R_3$ | $R_1$, $R_2$ | Haze (%) |
|---|---|---|---|
| 2 | —$CH_2CH{=}CH_2$ | —$CH_2CH_2CH_3$ | 4.5 |
| 3 | —$CH_2CH{=}CH_2$ | —$OCH_2CH_2CH_3$ | 4.6 |
| 5 | —$CH_2CH_2CH_3$ | —$CH_2CH_2CH_3$ | 4.6 |
| 6 | —$CH_2CH_2CH_3$ | —$OCH_2CH_2CH_3$ | 4.4 |
| Comparative 7 | —$CH_2CH{=}CH_2$ | —$CH_2CH_3$ | 5.2 |
| Comparative 8 | —$CH_2CH{=}CH_2$ | —$CH_3$ | 10.3 |
| Comparative 9 | —$CH_2CH{=}CH_2$ | —$CH_2CH_2CH_2CH_3$ | 6.0 |
| Comparative 10 | —$CH_2CH{=}CH_2$ | —$OCH_3$ | 12.0 |
| Comparative 11 | —$CH_2CH{=}CH_2$ | —$OCH_2CH_3$ | 7.6 |
| Comparative 12 | —$CH_2CH{=}CH_2$ | —$OCH_2CH_2CH_2CH_3$ | 12.8 |
| Comparative 13 | —$CH_2CH_2CH_3$ | —$CH_3$ | 9.6 |
| Comparative 14 | —$CH_2CH_2CH_3$ | —$CH_2CH_3$ | 5.6 |

US 2005-0239926A1 and US 2005-0239928A1 each disclose the compound of comparative example 7 above (allyl at R3 with ethyl at both R1/R2). The allyl with ethyl ($CH_2CH_3$) is the best performing of the comparative species shown above in terms of percent haze. However, invention examples 2, 3, 5, and 6 above all perform in a superior manner with regard to percent haze, even as compared to the allyl ethyl compound of comparative example 7. This greater performance is unexpected.

As shown in Table 1, the inventive compounds provide unexpected results in terms of significantly improved clarification performance comparing to comparative examples with similar chemical structures. In fact, the inventive compounds are believed to be the only such known compounds that offer less than about 5% haze in a 50 mils standard injection molded random copolymer polypropylene article at the concentration loading of 5000 ppm. This improved haze performance is very desirable, and could not have been predicted by a person of skill in the art.

For example, comparative examples 7, 8 and 9 where $R_3$=allyl and R1, R2=ethyl, methyl and n-butyl respectively, are similar structurally to invention compound example 2 (which employs propyl at both R1/R2). Invention compound example 2 employs a lower alkyl of n-propyl for $R_1R_2$, and therefore is "structurally between" ethyl and n-butyl in terms of the number of carbons of the lower alkyl. Unexpectedly, however, this compound example 2 provides significantly reduced haze as compared to its counterpart comparatives with both (1) more and (2) less carbons at the R1/R2 position. That is, the haze result is not between 5.2 and 6.0, as might be expected from review of the performance of the comparatives, but instead the haze of example 2 is well below 5.2. In fact, the haze of this inventive compound is only about 4.5. This unusually low haze value is unexpected. These findings are believed to represent a significant and unexpected discovery.

Given the structural similarity between the inventive compounds and comparative examples, these results are unexpected.

EXAMPLE 15

Taste Testing (Organoleptics)

This example demonstrates the low taste transfer characteristics of the compounds of the invention. When such compounds are used as plastic additives, it is important that the additive does not impart an undesirable taste to plastics, which are to be employed as food or beverage storage containers and the like. Organoleptic performance of DBS derivatives are believed to be determined by the aldehyde components.

The test protocol was set up modeled after the general guidelines established in: ASTM STP 434 (Manual on Sensory Testing Methods) and ASTM STP 758 (Guidelines for the Selection and Training of Sensory Panel Members). The experimental model is a statistically based method of pairwise comparison based on 95% or higher confidence limits.

Sample Preparation:

Additives are melt compounded into polypropylene by weighing and high intensity mixing. In addition to 3500 ppm of the clarifiers, the following additives are weighed and mixed into the polypropylene: 500 ppm Irganox 1010, 1000 ppm Irgafos 168, and 800 ppm calcium stearate. In this evaluation, the following clarifiers are added:

1. Example 2 at 3500 ppm
2. Example 3 at 3500 ppm
3. Comparative example 7 at 3500 ppm
4. Di(3,4-dimethylbenzaldehyde)sorbitol (commercial Millad 3988®) at 2000 ppm. The resin samples are then melt compounded on a single screw extruder, and formed into pellets. The pellets are injection molded into plaques measuring 0.050 inches thick by 2.0 inches wide by 3.0 inches long.

Sample Treatment:

Water has been found to be the best media to perform organoleptic evaluations as it imparts the least taste to the panelist in order to minimize interferences with the material being tested. Samples of the compounded and molded polypropylene resin are placed in clean glass jars separated by glass pipettes and covered with water. The typical surface to volume ratio used for the samples is 675 $cm^2/1$. The containers are securely sealed and aged in an oven for about five days at 50° C. The resulting water is then chilled for sensory panel evaluation.

Panelist's Evaluation:

Tap water is provided for each panelist to clear the palate before and in between each tasting. Possible bias of sample tasting order is removed by balancing the design with respect to the order of presentation in a pair (each additive appears equally first and second in the tasting). In addition, the order of the pairs presented in the tasting session is randomized for the panelists. Thus, the experimental design attempts to remove sources of possible design bias and the experiment protocol and test conditions attempt to reduce other sources of bias and interference. The experiment is double blind so that neither the panelist nor the testing facilitator knows the identity of the samples being tested.

Statistical Analysis:

The results of the testing are statistically analyzed using *The Method of Pairwise Comparison* by Herbert A. David. A 95% confidence level is used for the evaluation of the data. Depending on the experimental design, each additive must have a separation of a required number of units in order to be considered statistically different at the 95% confidence level. The sample designs and required separation unit at the 95% confidence level are given below.

TABLE 2

Experimental Designs for Organoleptic Evaluations

| Number of Samples Being Tested | Minimum Number of Panelists Required for Test | Number of Pairs to be Tested Per Panelist | Number of Sittings Required | Differences Between Responses to be Considered Statistically Significant at 95% Probability Level |
|---|---|---|---|---|
| 2 | 15 | 1 | 1 | 7 |

In this evaluation, samples 2,3, and comparative example 7 are individually compared to Millad® 3988 in a pairwise comparison as described, with 15 panelists. The results are as follows:

EXAMPLE 2 ORGANOLEPTIC RESULTS

Millad 3988® was chosen as having the least taste over the compound of example 2 by a score of 8-7 (that is 8 panelists chose Millad 3988 as having the least taste while 7 panelists chose sample 2 as having the least taste), which is not statistically significant at the 95% confidence interval. Thus, in addition to outstanding haze levels, example 2 has acceptable organoleptics.

EXAMPLE 3 ORGANOLEPTIC RESULTS

Millad 3988® was chosen as having the least taste over example 3 by a score of 10-5 (that is 10 panelists chose Millad 3988 as having the least taste while 5 panelists chose sample 3 as having the least taste), which is not statistically significant at the 95% confidence interval. Thus, in addition to the outstanding haze levels, example 3 has acceptable organoleptics.

EXAMPLE 5 ORGANOLEPTIC RESULTS

Millad® 3988 was chosen as having the least taste over example 5 by a score of 10-5 (that is 10 panelists chose Millad® 3988 as having the least taste while 5 panelists chose example 5 as having the least taste), which is not statistically significant at the 95% confidence interval. Thus, in addition to outstanding haze values, example 5 has acceptable organoleptics.

COMPARATIVE EXAMPLE 7 ORGANOLEPTIC RESULTS

Millad 3988® was chosen as having the least taste over the comparative example 7 by a score of 15-0 (that is 15 panelists chose Millad 3988 as having the least taste while 0 panelists chose the comparative example 8 as having the least taste), which is statistically significant at the 95% confidence interval. Thus, the comparative example 7 (the compound with R3 as allyl and R1/R2 as ethyl) provides unacceptable organoleptics (for food contact container applications).

Millad 3988®, which offers excellent organoleptic performance, is the leading commercial clarifier. Its organoleptic performance is considered as the standard of polyolefin clarifier industry. A clarifier that is not statistically different from Millad 3988® in the taste study is considered adequate in organoleptic performance, whereas a clarifier that is statistically different from Millad 3988® is considered less than desirable for many commercial applications. The data suggests that the inventive examples are comparable in organoleptic performance to Millad 3988®, and the comparative Example 7 (allyl, p-ethyl compound) is less desirable and likely not fit for use in a wide range of applications.

Given the structural similarity between the inventive compounds and comparative examples, the results of organoleptic performance for compounds of the invention are unexpected and beneficial.

EXAMPLE 16

Yellowness Index in Controlled Rheology (CR) Resin

Controlled rheology (CR) is a process used in the manufacture of polypropylene to decrease the average molecular weight of the polymer. The decrease results in an increase in melt flow rate and a number of processing benefits such as fast cycle time, better flow properties and improved mold filling. CR process is typically conducted by introducing peroxides, which act as catalysts to degrade polypropylene, under a controlled condition to product a polymer with unique and desirable molecular weight distribution. Certain clarifiers might interact with the peroxides and result in an increase in undesirable yellowing. Yellowing is undesirable in commercial applications.

Compositions containing comparative examples 5, 6 and comparative example 7 each were separately mixed with 1000 grams of an 11 MFR (Melt Flow Rate or Index) polypropylene random copolymer resin (RCP, 3% ethylene content) and standard additive package (i.e. 500 ppm Irganox 1010, 1000 ppm Irgafos 168, and 800 ppm Calcium Stearate, CaSt) using a Gardner ribbon blender for five minutes at approximately 200-220 rpm. The blend was then melt compounded on a Prism 16 mm diameter, 25:1 L/D co-rotating twin screw extruder. Lupersol® 101 (2,5-dimethyl-2,5-di-t-butylperoxy hexane; Atofina Chemicals) were introduced to the polyproylene melt during extrusion process. The pellets were collected. The melt flow rate and yellowness index of the resulting pellets were measured. The yellow index was measured on a Gretag MacBeth Coloreye 6000 according to ASTM E313-73. The data is listed in Table 3.

TABLE 3

Yellowness Index Testing

| Polymer | Example | Concentration (ppm) | Yellowness Index |
|---|---|---|---|
| RCP PP | Millad 3988 ® | 2000 | −0.394 |
| RCP PP | Millad 3988 ®/Lupersol 101 | 2000/500 | −0.094 |
| RCP PP | 5 | 3500 | −0.605 |
| RCP PP | 5/Lupersol 101 | 3500/500 | −0.511 |
| RCP PP | 6 | 3500 | −0.400 |
| RCP PP | 6/Lupersol 101 | 3500/500 | −0.511 |
| RCP PP | 7/Lupersol 101 | 3500/500 | 4.338 |

The results clearly show the inventive compounds of inventive examples 5 and 6 display excellent color (low yellowness) while the comparative example 7 (allyl; ethyl) displays a tendency to yellow during CR process. Such yellowing is undesirable. Given the structural similarity between the inventive compounds (i.e. R1/R2 as n-propyl for example 5 and R1/R2 as n-propoxy for example 6) and the comparative example (R1/R2 as ethyl), such advantageous non-yellowing results are unexpected and desirable.

It should understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

The invention claimed is:

1. A compound of:

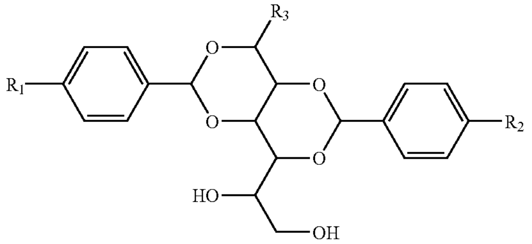

wherein $R_1$ and $R_2$ are independently selected from the group consisting of: $CH_3CH_2CH_2$— and $CH_3CH_2CH_2O$—; and wherein $R_3$ is independently selected from the group of: —$CH_2CH_2CH_3$ and —$CH_2$—$CH{=}CH_2$.

2. The compound of claim 1, wherein $R_3$ is —$CH_2CH_2CH_3$.

3. The compound of claim 1, wherein $R_3$ is —$CH_2$—$CH{=}CH_2$.

4. A compound:

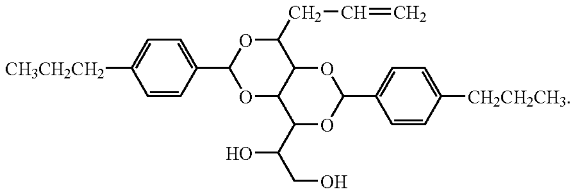

5. A compound:

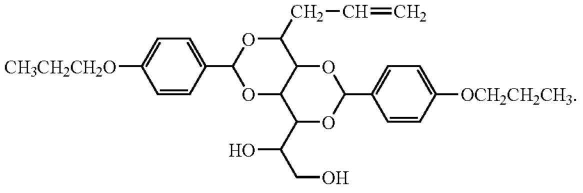

6. A compound:

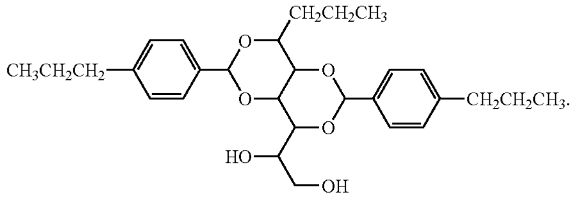

7. A compound:

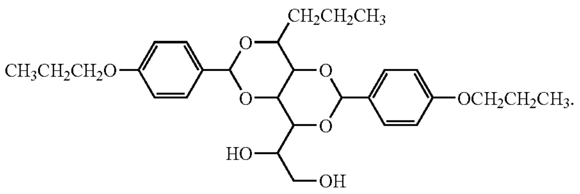

8. A nucleating or clarifying composition comprising a compound of claim 1.

9. A polyolefin composition comprising a compound of claim 1 combined with an olefin polymer.

10. An article of manufacture comprising the polyolefin composition of claim 9.

11. A method of clarifying an olefin polymer by combining an olefin polymer with a compound as set forth:

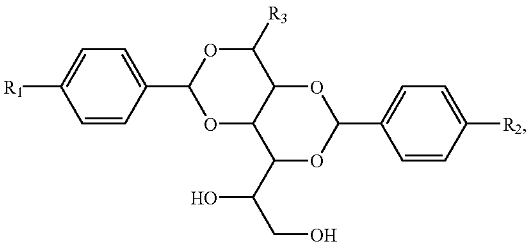

I wherein $R_1$ and $R_2$ are independently selected from the group consisting of: $CH_3CH_2CH_2$— and $CH_3CH_2CH_2O$—; and wherein $R_3$ is independently selected from the group of: —$CH_2CH_2CH_3$ and —$CH_2$—$CH$═$CH_2$.

* * * * *